United States Patent
Van Groenestijn et al.

(10) Patent No.: US 9,435,077 B2
(45) Date of Patent: Sep. 6, 2016

(54) METHOD FOR PROCESSING LIGNOCELLULOSE CONTAINING MATERIAL

(75) Inventors: Johannes Wouterus Van Groenestijn, Apeldoorn (NL); Jan Matthijs Jetten, Zeist (NL); Hendricus Cornelis Van Deventer, Apeldoorn (NL); Ronald Slomp, Delft (NL); Theodoor Maximiliaan Slaghek, Rotterdam (NL)

(73) Assignee: NEDERLANDSE ORGANISATIE VOOR TOEGEPAST-NATUURWETENSCHAPPELIJK ONDERZOEK TNO, Delft (NL)

( * ) Notice: Subject to any disclaimer, the term of this patent is extended or adjusted under 35 U.S.C. 154(b) by 0 days.

(21) Appl. No.: 13/514,944

(22) PCT Filed: Dec. 10, 2010

(86) PCT No.: PCT/NL2010/050840
§ 371 (c)(1),
(2), (4) Date: Jul. 26, 2012

(87) PCT Pub. No.: WO2011/071386
PCT Pub. Date: Jun. 16, 2011

(65) Prior Publication Data
US 2012/0282660 A1 Nov. 8, 2012

(30) Foreign Application Priority Data
Dec. 11, 2009 (EP) .................................... 09178978

(51) Int. Cl.
| | | |
|---|---|---|
| C12P 19/02 | (2006.01) | |
| D21C 1/02 | (2006.01) | |
| C08B 1/00 | (2006.01) | |
| C08B 1/02 | (2006.01) | |
| C08B 1/06 | (2006.01) | |
| C08H 1/00 | (2006.01) | |
| C08H 1/06 | (2006.01) | |
| C08H 8/00 | (2010.01) | |
| C12P 7/10 | (2006.01) | |
| D21B 1/02 | (2006.01) | |
| D21B 1/12 | (2006.01) | |
| D21C 1/04 | (2006.01) | |
| D21C 1/06 | (2006.01) | |

(52) U.S. Cl.
CPC . *D21C 1/02* (2013.01); *C08B 1/00* (2013.01); *C08B 1/02* (2013.01); *C08B 1/06* (2013.01); *C08H 1/00* (2013.01); *C08H 1/06* (2013.01); *C08H 8/00* (2013.01); *C12P 7/10* (2013.01); *D21B 1/021* (2013.01); *D21B 1/12* (2013.01); *D21C 1/04* (2013.01); *D21C 1/06* (2013.01); *C12P 2201/00* (2013.01); *C12P 2203/00* (2013.01); *Y02E 50/16* (2013.01)

(58) Field of Classification Search
None
See application file for complete search history.

(56) References Cited

U.S. PATENT DOCUMENTS

| | | | |
|---|---|---|---|
| 5,328,562 A | 7/1994 | Rafferty et al. | |
| 5,473,061 A | 12/1995 | Bredereck et al. | |
| 6,660,506 B2 | 12/2003 | Nguyen et al. | |
| 6,765,042 B1 * | 7/2004 | Thornton et al. | 523/400 |
| 2003/0044951 A1 * | 3/2003 | Sporleder et al. | 435/198 |
| 2007/0031953 A1 * | 2/2007 | Dunson et al. | 435/161 |
| 2007/0249824 A1 | 10/2007 | Shikata | |
| 2009/0258404 A1 * | 10/2009 | Mikkelsen et al. | 435/139 |

FOREIGN PATENT DOCUMENTS

| | | |
|---|---|---|
| DE | 831322 | 2/1952 |
| DE | 4329937 | 11/1994 |
| EP | 0052489 | 5/1982 |
| GB | 127388 | 5/1919 |
| GB | 349032 | 5/1931 |
| GB | 491842 | 9/1938 |
| GB | 541960 | * 12/1941 |
| GB | 674079 | 6/1952 |

OTHER PUBLICATIONS

Karimi et al., Biomass and Bioenergy, 30: 247-253 (2006).*
Deejing et al., Chiang Mai J. Sci., 36(3):384-394 (2009).*
Mosier et al., Bioresource Technology 96:673-686 (2005).*
Oriol et al., Appl. Microbiol. Biotechnol., 27:498-503 (1988).*
Kling et al., Biotech. Bioeng. 29:1035-1039 (1987).*
Lamptey et al., Biotechnol. Let., 7(7):531-534 (1985).*

* cited by examiner

*Primary Examiner* — Thomas J Visone
(74) *Attorney, Agent, or Firm* — Lucas & Mercanti, LLP.

(57) ABSTRACT

The invention is related to a method for processing biomass derived from plants or animals, comprising the steps of:
 a. pre treating said material with an aqueous solution of acid or base;
 b. subsequently passaging saturated or super heated steam through said material,
wherein the water activity of the process is controlled by means of temperature and pressure of the super heated steam to be less than 1, preferably less than 0.8, more preferably in the range of 0.4-0.8.
With such a process it is possible to disintegrate or make more accessible for subsequent treatments the lignocellulose from lignocellulose containing materials, like wood or other plant material, chitin from exoskeletons from Crustacea like crabs and shrimps, and proteins such as keratin from pig hair or chicken feather, for further derivation, like acylation, oxidation, etherification, carboxymethylation or esterification, or further enzymatic hydrolysis, and/or for production of chemicals, e.g. as sugars from carbohydrates for fermentation processes such as the production of (bio-) ethanol or as keratine hydrolysates for applications in paper or cosmetics.

20 Claims, 3 Drawing Sheets

METHOD FOR PROCESSING LIGNOCELLULOSE CONTAINING MATERIAL

CROSS-REFERENCE TO RELATED APPLICATIONS

Figure 1:
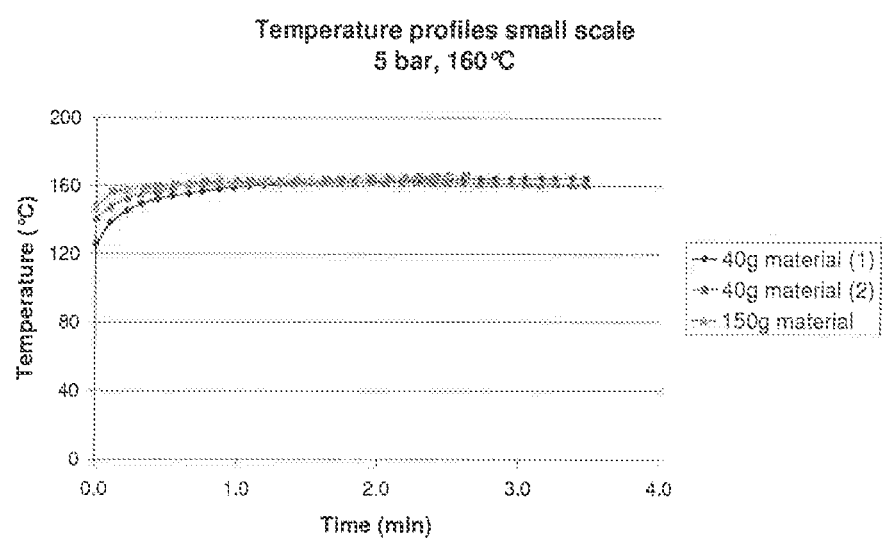

This application is a 371 of PCT/NL2010/050840 filed Dec. 10, 2010, which claims the benefit of European Patent Application No. 09178978.4 filed Dec. 11, 2009, the contents of each of which are incorporated herein by reference.

FIELD OF THE INVENTION

The invention relates to the field of processing of raw materials, especially raw plant- or animal-derived materials. More specifically, the invention relates to disintegration of lignocellulose from lignocellulose containing materials, like wood or other plant material, chitin from exoskeletons from Crustacea like crabs and shrimps, and proteins such as keratin from pig hair or chicken feather for production of chemicals, e.g. as sugars from carbohydrates for fermentation processes such as the production of (bio)ethanol or as keratin hydrolysates for applications in paper or cosmetics. Even more specifically, the present invention relates to those processes in which superheated steam is brought in direct contact with raw materials in a single processing step.

BACKGROUND OF THE INVENTION

Lignocellulosic biomass refers to plant biomass that is composed of cellulose, hemicellulose, and lignin. This biomass comes in many different types, which may be grouped into four main categories: (1) wood residues (including sawmill and paper mill discards), (2) municipal paper waste, (3) agricultural residues (including corn stover and sugarcane bagasse), and (4) dedicated energy crops (which are mostly composed of fast growing tall, woody grasses). In all these categories the carbohydrate polymers (cellulose and hemicelluloses) are tightly bound to the lignin, by hydrogen and covalent bonds.

Fermentation of lignocellulosic biomass to ethanol and butanol is an attractive route to process energy feedstocks that supplement the depleting stores of fossil fuels. Biomass is a carbon-neutral source of energy, since it comes from dead plants, which means that the combustion of ethanol produced from lignocelluloses will produce no net carbon dioxide in the earth's atmosphere. Also, biomass is readily available, and the fermentation of lignocelluloses provides an attractive way to dispose of many industrial and agricultural waste products. Finally, lignocellulosic biomass is a renewable resource. Many of the dedicated energy crops can provide high energy biomass, which may be harvested multiple times each year.

One barrier to the production of ethanol from biomass is that a large fraction of the sugars necessary for fermentation present in the form of lignocellulose. Lignocellulose has evolved to resist degradation and to confer hydrolytic stability and structural robustness to the cell walls of the plants. This robustness or "recalcitrance" is attributable to the crosslinking between the polysaccharides (cellulose and hemicellulose) and the lignin via ester and ether linkages, thus creating a material that is physically hard to access. This means that for an efficient use of the components from the lignocellulose, said lignocellulose should be disintegrated and/or separated and/or decrystallized, to allow enzymes to be able to contact the cellulose and hemicellulose for conversion into oligo- and monosaccharides, which then in turn can be used for many purposes, e.g. for bio-ethanol formation and further derivation.

One of the most commonly used methods for degradation of the lignocellulose is heating of the wet biomass in the presence of an acid. Two major problems occur with such a treatment: 1) the heating may only be short, because otherwise too many unwanted byproducts are formed from the carbohydrates; and 2) it is difficult to produce a biomass slurry with more than 30% w/w solids, which is necessary for an economic use in further processing.

Accordingly there is still need for an efficient process in which lignocellulose is degraded to disclose the components thereof for further processing.

SUMMARY OF THE INVENTION

The present invention now overcomes the disadvantages of the prior art. Accordingly, the invention relates to a method for processing biomass derived from plants or animals, comprising the steps of:
  a. pre treating said material with an aqueous solution of acid or base;
  b. subsequently passaging saturated or super heated steam through said material,
whereby the water activity of the process is controlled by means of temperature and pressure of the super heated steam to be less than 1, preferably less than 0.8, more preferably between 0.4-0.8.

In a preferred embodiment, the acid is sulphuric acid ($H_2SO_4$) or the base is chosen from the group consisting of calcium hydroxide, sodium hydroxide and potassium hydroxide, ammonium hydroxide or the acid or base is any in situ formed acid or base. Preferably the acid is provided in a solution of about 0.1% to about 4.0%, preferably about 0.5% to about 3.0%, more preferably about 2%. When a base is used, preferably the base is mixed with biomass in a ratio of 0.02 to 0.2 grams base per gram biomass dry matter, preferably in a ratio of 0.15.

In yet another preferred embodiment step a) is performed at a temperature of about 20 to about 80° C., more preferably at a temperature of about 50 to about 65° C. Further preferred is a method according to the invention, wherein the super heated steam is applied under a pressure between 1 and 10 bara, preferably between 4 and 8 bara, more preferably around 6 bara. Further preferred is a method according to the invention, wherein the temperature of the super heated steam is between 150 and 220° C., preferably between 160 and 200° C., more preferably between 170 and 180° C.

In yet another preferred embodiment the method according to the invention comprises a further step c) of further enzymatic hydrolysis (exo and endo activity), oxidation, etherification or esterification of said material after SHS treatment.

Further preferred in a method according to the invention the biomass material is woody plant material, including leaves, twigs, bark, grasses, hay, reeds, megasse, straw, wood chips, sawdust, bagasse, corn stover, corn cobs, wheat bran, sugar beet press cake, rice hulls, palm, coconut, cotton fibres and/or peat, sphagnum, filtercake from sewage plants, sewage effluents, animal waste, like feathers and hairs, or crystalline cellulose.

LEGENDS TO THE FIGURES

FIG. 1. Temperature profile during small scale experiments (different loadings).

Figure 2:
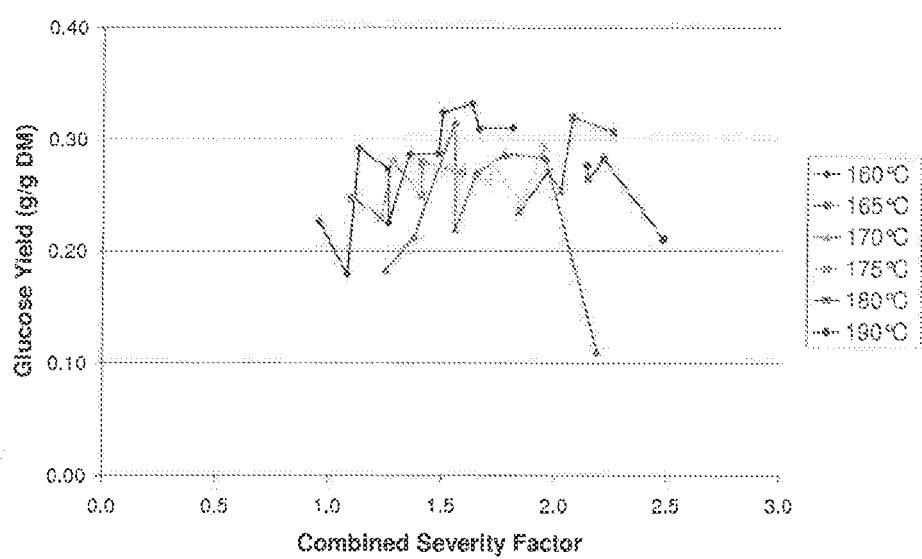

FIG. 2. Glucose recovery after SHS treatment where the treatment conditions are represented by the Combined Severity Factor (for explanation, see text).

Figure 3:
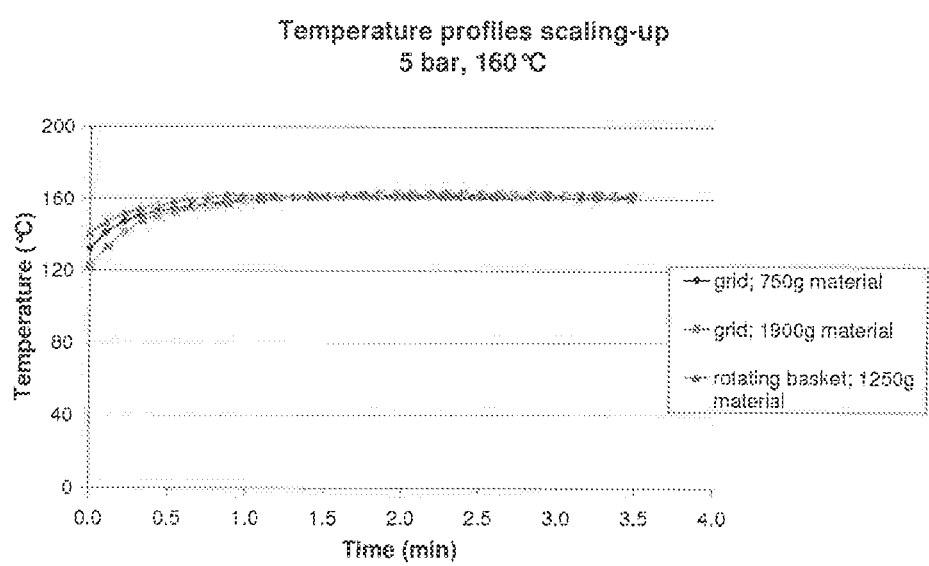

FIG. 3. Temperature profile during scaling-up experiments (different loadings).

DEFINITIONS

"Lignocellulosic biomass" refers to plant biomass that is composed of cellulose, hemicellulose, and lignin.

"Super Heated Steam" (SHS) is steam that is (indirectly) heated to a temperature above its evaporation temperature. When water is heated it evaporates to steam at the boiling temperature of water to form steam. For example at atmospheric pressure the boiling temperature of water is 100° C.; for higher pressures the boiling temperature increases. This steam is still at the boiling temperature and it is called saturated steam. When saturated steam cools down it immediately condenses to water.

When however this saturated steam is heated, the temperature increases while the pressure stays the same. This is called Super Heated Steam, SHS, or dry steam. This SHS can cool down without immediate condensation. Only when the SHS is cooled down until the boiling temperature of water at the given pressure, it will start to condense.

The "water activity" or "Aw" of SHS as a processing medium can be controlled by varying the pressure and the superheating temperature. The Aw of SHS is the defined as the actual absolute pressure of the SHS divided by the pressure that saturated steam would have at that actual temperature of the SHS.

In formula:

$$A_w = P_{SHS}/P_{saturated\ steam\ at\ T\ SHS}$$

(P=absolute pressure)
Some examples:

| Absolute pressure SHS (bar) | Temperature SHS (° C.) | Absolute pressure saturated steam at temperature SHS (bar) | Aw |
| --- | --- | --- | --- |
| 1 | 120 | 2 | ½ = 0.50 |
| 1 | 144 | 4 | ¼ = 0.25 |
| 1 | 159 | 6 | ⅙ = 0.17 |
| 1 | 180 | 10 | 1/10 = 0.10 |
| 2 | 144 | 4 | 2/4 = 0.50 |
| 2 | 159 | 6 | 2/6 = 0.33 |
| 2 | 180 | 10 | 2/10 = 0.2 |
| 4 | 159 | 6 | 4/6 = 0.67 |
| 4 | 180 | 10 | 4/10 = 0.40 |
| 6 | 180 | 10 | 6/10 = 0.60 |

This makes SHS unique over hot air, where the Aw value is always very low, normally below 0.01

"Treatment severity" is defined as the extent in which reactive and destructive conditions are present.

The "combined severity factor" or "CSF" describes the severity of various acid-catalyzed pretreatments by combining time, temperature and acid concentration. The combined severity factor (CSF) is given by:

$$CSF = \log_{10}\{t_r \cdot \exp[(T_r - 100)/14.75]\} - pH$$

in which $T_r$ is the reaction temperature in degrees Celsius and $t_r$ is the reaction time in minutes. The pH value is calculated from the sulphuric acid concentration inside the fibers at the beginning of the treatment (pre-impregnated material).

DETAILED DESCRIPTION

Heating a lignocellulose slurry to degrade it and make the individual components available for further processing has been performed in several ways in the prior art. Consequently, methods of applying heat to the material with super heated steam (SHS) have been known for a long time. As a matter of fact, one of the earliest disclosures of such a method is GB 127,388 from 1918 (!), in which a process is described for making fodder from e.g. peat moss or sphagnum, which involves an acid treatment of the biomaterial in an autoclave at relatively low pressure while heating (drying) with SHS. The main difference between this publication and the present invention is the fact that in GB 127,388 no pretreatment with acid is performed and that the steam is applied in a closed vessel and not in a system in which the steam is led through the material.

A drying action of SHS similar to the one used in the present invention is also described in GB 541,960. However, in this document no acid treatment is used to disintegrate the biomaterial, but instead the material is soaked with (normal, saturated) steam under high pressure. A similar system is described in U.S. Pat. No. 5,328,562 in which a two stage process of first heating the wet biomaterial under pressure followed by drying with SHS is used to produce hydrolysed biomaterial. It appears that hydrolysis is meant to take place without addition of any chemicals.

Another treatment with SHS is described in GB 491,842, but here the biomaterial is (pre)treated with (caustic) soda and not with acid.

A process which resembles the process of the invention is described in GB 349,032 wherein wood chips are impregnated with sulphuric acid and then subjected to SHS treatment. The main difference is that this process basically starts from cellulose and not lignocellulose, which implies that the goal of the treatment is not degradation of lignocellulose and disclosure of the components thereof, but reaction of cellulose into sugars. The acid pretreatment is effected with a large volume of a dilute (0.25-1%) acid solution, after which the bulk of the acid solution is removed and the reaction is continued for several hours under elevated pressure at a temperature of about 150° C. which is maintained by passing SHS through the material. Thus, although similar steps are applied in this process, the goal is different and differences in the process temperature and duration are apparent and explainable for this different goal.

A further prior art document is US 2003/199049 (patented as U.S. Pat. No. 6,660,506). This document describes a process in which biomass is impregnated with acid and wherein said biomass is dried with e.g. SHS, after which a heated hydrolysis takes place. The difference between the process as described in this document with the current invention is that the steps of drying and hydrolysis in the current invention take place simultaneously in one and the same reactor. The combination of these steps gives the advantage of a gradual increase in temperature which causes first the hemicellulose to be degraded and then the cellulose to decrystallize.

There are many prior art documents that apply steam at high temperature to a biomass, which is either pre-treated or not, but just application of the SHS only influences the surface of the biomass that is contacted. In the present invention the effect of the SHS is increased by the fact that the SHS is passaged through the biomass, meaning that the effect of the SHS treatment also is provided within the biomass. The effect is of course even more increased if the structure of the biomass is such that the SHS can easily reach the non-superficial parts. Thus a porous structure of the biomass or a very loose packing of the biomaterial greatly enhances the drying effect of the SHS.

Although the invention is mainly directed to biomass comprising lignocellulose, any biomass comprising lignocellulose, cellulose, hemi cellulose, lignin, proteins like chitin, keratin, carbohydrates like starches or the like and wherein the mentioned compounds need to be made more accessible for subsequent treatments may be processed.

According to the invention the lignocellulose containing material is impregnated with acid or base.

As acid or base in principle any inorganic or organic acid or base would be usable, but for economical reasons strong acids are preferred because even a diluted solution of such strong acids has sufficient hydrolytic action to be able to disclose the polysaccharides from the lignocellulose material. Further, since the acid treatment is preferably performed under an elevated temperature (from about 20° C. to about 200° C.) the acid solution should remain stable in this temperature range. Most preferably sulphuric acid is used. The acid is added to provide a final concentration of about 0.1% to 4% (but this can vary even further based on the particular acid used). For sulphuric acid preferably about 0.5% to about 3.0%, more preferably about 2% is used.

As base preferably a hydroxide is used, such as calcium hydroxide, sodium hydroxide or potassium hydroxide or ammonia hydroxide.

Further as acid or base any in situ formed acid (such as acetic acid) or base within the said process can be applicable.

Incubation of the biomaterial with the acid or base is performed for about 1 hour to about 24 hours. The optimal incubation time depends on the openness of the material: the more loosely the material is packed, the less incubation time is needed. For straw an optimal incubation time is approximately three hours. Wood will require longer incubation periods and these will depend on the size of the wood chips used.

Incubation with acid or base is also preferably performed at an elevated temperature. Generally the process will satisfactorily run at a temperature of about 20° C. to about 80° C., more preferably at a temperature of about 50° C. to about 65° C.

After incubation, the slurry consisting of the biomaterial and the acid or basic solution is then placed in a steam process or, more generally defined, in a surrounding, preferably a closed surrounding, in which super heated steam can be led through the biomass. The whole disintegration process with SHS is preferably performed under an increased pressure. During this disintegration process in SHS also drying takes place, thus resulting in a disintegrated biomass with a lower water content. It can be performed under atmospheric pressure (1 Bara) up to 10 Bara, but preferably is performed under a pressure of 2-7 Bara, more preferably 6 Bara.

Steam with a temperature of between about 150° C. and 220° C. (super heated steam, SHS) is produced and led through the chamber with the biomass. Preferably steam of about 170° C.-180° C. is used. As is the case with the acid incubation, also here the time that is needed to disintegrate the biomass with the SHS depends on the openness of the biomass: the less densely packed, the more opportunity there is for the steam to reach the surface of the biomass material, and the quicker the disintegration and drying process will occur. When the steam is applied, the biomass quickly warms up to the condensation temperature of the steam at the given pressure, for example at 6 bara at about 159° C. It will keep this temperature for a certain time as long as the surface of the biomass is still wet. When, due to the drying effect of SHS, the surface falls (locally) dry, the biomass will heat up further to a higher level. Application of steam is continued at this higher level for about 1 to 10 minutes, more preferably 1 to 5 minutes. After that, the application of steam is stopped, if necessary the pressure is returned to atmospheric pressure by opening the pressure chamber, and the biomass is allowed to cool down.

During the drying step of the process the Aw is preferably kept constant. This allows the application of higher temperatures (which, in turn, will result in a better liberation and hydrolysis) and also would allow for a minimalisation of the acid needed for the process. The Aw can easily be kept constant in SHS by keeping both the pressure and the SHS temperature constant. Preferably the Aw of the process is controlled by means of temperature and pressure of the super heated steam to be less than 1, preferably less than 0.8, more preferably in the range of 0.4-0.8.

During drying of the acid or base soaked biomass, the hydrolysis of the lignocellulose continues in a unique manner: because the acid or base concentration increases due to the evaporation of water and the temperature increases during this process, first the hemicellulose (which is located at the outside of the lignocellulose fibers) is—partially— degraded, then the bonds between lignin and polysaccharides are broken after which the remaining cellulose is decrystallized.

Thus, the above described process results in a biomass in which the polysaccharides are liberated from the lignocellulose complex and will be freely available for further hydrolysis, e.g. through addition of cellulose and/or lignin-degrading enzymes, or derivations or functionalization by means of acylation, oxidation, esterification, etherification, carboxymethylation and so on. In the Examples it is shown that because of the higher liberation rate of the polysaccharides, the yields of the further derivations/functionalizations is higher with a biomass preprocessed according to the invention.

Further, advantageously, it has appeared possible to reach higher dry solid weight contents (ranging from 25-65%) in the resulting biomass slurry, which makes it possible to feed subsequent fermentations with highly concentrated material and reach high titers of the desired fermentation product (e.g. in a fed batch simultaneous saccharification and fermentation process). This is also advantageous for the further processing, because less water has to be removed from the biomass slurry. It has further appeared that enzymatic hydrolysis after this new method for pretreatment of lignocellulose is very effective and yields of more than 90% conversion into glucose and xylose can be obtained. The obtained xylose can be reduced and used for the production of xylitol. Further, some byproducts that would hamper the further hydrolysis and fermentation, like furfural, HMF, acetic acid and levulinic acid are absent from or only present in low quantities in the resulting biomass slurry.

EXAMPLES

Example 1

Wheat Straw Biomass

Before superheated steam treatment the dried wheat straw (12 hrs 95° C.) was pre-impregnated in a $H_2SO_4$ solution for 3 hours at 60° C. and 8% dry matter concentration to obtain the desired $H_2SO_4$ concentration inside the fibres. After impregnation free liquid was removed by filtration.

All steam treatments were carried out at 6 bara in the TNO pilot laboratory super heated steam equipment. After inserting wheat straw into the steam equipment this pressure can immediately be reached. For exploring the effect of reaction conditions, different temperatures, sulphate concentrations and heating times were applied. The effect of the treatment on the accessibility of the polysaccharides was tested by enzymatic hydrolysis. To avoid product inhibition during the hydrolysis, the dry matter was diluted with water. This dilution was only carried out for determination purposes.

Samples of approximately 45 gram impregnated wheat straw were used (±10 gram dry matter). After steam drying water was added to the samples to obtain 5% dry matter concentrations. With calcium hydroxide the pH was adjusted to 5. Enzyme loading was 0.24 ml GC220 (a mixture of cellulose and hemicellulases from Genencor) and 0.018 ml NS50010 (cellobiase form Novozymes) per gram dry matter. 10 ml penstrep per liter hydrolysate was added and the enzymatic hydrolysis was performed for 3 days at 50° C.

For scaling-up two configurations were used. First a grid covered with a thick bed of wheat straw was used. Maximum load to cover the grid was 2000 gram impregnated wheat straw (±470 g dry matter). Then a rotating basket was used to mix the wheat straw arranging equal conditions for the complete sample. Maximum load was 1250 gram impregnated material (±250 g dry matter). Conditions found to be optimal during the small scale experiments were applied during scaling-up. After superheated steam treatment a small fraction of the wheat straw was used for hydrolysis. Hydrolysis was performed in the same way as described for the small scale experiments.

To determine efficiencies, glucose was measured via an enzymatic assay. Other monosaccharides and organic acids were measured with gas chromatography-mass spectrometry (GC-MS). HMF and furfural were measured with solid-phase microextraction (SPME).

1.1.1 Results Small Scale Experiments

To determine the temperature during superheated steam treatments the temperature inside the reactor was measured. An example is given in FIG. 1.

During treatments the required temperature was reached after 30 seconds at about 160° C. The temperature in the reactor is depicted in FIG. 1. The temperature inside the fibers can follow a different pattern; fast heating till 159° C. (boiling temperature at 6 bara) followed by evaporation of water and inherent increase of temperatures.

Table A gives the results for various SHS conditions, using previous experience gained with autoclave experiments. Sulphuric acid concentrations were comparable with dilute acid autoclave pretreatments (1.5-3% $H_2SO_4$). The wheat straw samples contained approximately 20% dry matter after pre-impregnation. The glucose content of wheat straw used for these experiments was 0.343 g/g DM (determined with the method described by Cao et al., 1997), which was the theoretical maximum.

TABLE A

Small scale SHS treatments, sulphate concentrations between 1.5 and 3%

| SHS conditions | | | After SHS treatment | | |
|---|---|---|---|---|---|
| Temp. (° C.) | Time (min) | H2SO4 (%) | H2SO4 (%) | Dry matter (%) | Glucose yield (g/g DM) |
| 155 | 1.5 | 1.5 | 2.9 | 19 | 0.27 |
| " | " | 2.0 | 3.6 | 22 | 0.29 |
| " | " | 3.0 | 4.8 | 24 | 0.29 |
| 160 | 1 | 1.5 | 3.4 | 25 | 0.23 |
| " | " | 2.0 | 4.0 | 26 | 0.18 |
| " | " | 3.0 | 5.3 | 27 | 0.23 |
| 160 | 1.5 | 1.5 | 3.2 | 28 | 0.29 |
| " | " | 2.0 | 4.1 | 32 | 0.27 |
| 160 | 2.5 | 1.5 | 3.2 | 27 | 0.29 |
| " | " | 2.0 | 3.9 | 30 | 0.29 |
| " | " | 3.0 | 4.7 | 28 | 0.31 |
| 160 | 3.5 | 1.5 | 3.1 | 21 | 0.32 |
| " | " | 2.0 | 4.4 | 29 | 0.33 |
| " | " | 3.0 | 4.7 | 24 | 0.31 |
| 165 | 1 | 1.5 | 3.3 | 29 | 0.25 |
| " | " | 2.0 | 4.2 | 33 | 0.23 |
| " | " | 3.0 | 4.8 | 28 | 0.28 |
| 165 | 1.5 | 1.5 | 3.4 | 26 | 0.28 |
| " | " | 2.0 | 4.3 | 28 | 0.25 |
| " | " | 3.0 | 5.7 | 29 | 0.27 |
| 170 | 1 | 1.5 | 3.9 | 30 | 0.18 |
| " | " | 2.0 | 4.5 | 30 | 0.21 |
| " | " | 3.0 | 5.3 | 27 | 0.22 |
| 170 | 1.5 | 2.0 | 4.0 | 28 | 0.32 |
| 170 | 2.5 | 1.5 | 4.0 | 37 | 0.27 |
| " | " | 2.0 | 4.6 | 37 | 0.29 |
| " | " | 3.0 | 6.4 | 38 | 0.28 |
| 170 | 6.5 | 2.0 | 4.1 | 29 | 0.11 |
| 175 | 1.5 | 2.0 | 6.2 | 48 | 0.26 |
| 175 | 3.5 | 1.5 | 8.0 | 56 | 0.29 |
| " | " | 2.0 | 6.8 | 44 | 0.32 |
| " | " | 3.0 | 10.0 | 47 | 0.31 |
| 180 | 1.5 | 1.5 | 4.6 | 37 | 0.28 |
| " | " | 2.0 | 4.8 | 32 | 0.24 |
| " | " | 3.0 | 6.2 | 32 | 0.25 |
| 180 | 3.5 | 2.0 | 12.3 | 65 | 0.28 |
| 180 | 6.5 | 2.0 | 11.0 | 62 | 0.21 |
| 190 | 1 | 1.5 | 5.0 | 40 | 0.24 |
| " | " | 2.0 | 4.9 | 33 | 0.27 |
| " | " | 3.0 | 6.2 | 32 | 0.26 |
| 190 | 1.5 | 2.0 | 7.1 | 49 | 0.28 |

The water activities in this experiment ranged from 0.47 (at 190° C.) via 0.75 (at 170° C.) and 0.97 (at 160° C.) to 1.0 (at 155° C.), all at 6 bara pressure. After SHS treatment the dry matter concentration increased. Higher reaction temperatures gave more evaporation of water and higher sulphate and dry matter concentrations. Increasing dry matter concentration is advantageous for the economy of fermentation processes—increasing dry matter gives higher sugar and subsequently ethanol concentrations.

Temperatures ranging from 155 till 190° C. can be applied to obtain glucose yields above 0.28 g/g DM. Variation of the sulphate concentration (1.5 to 3%) or the reaction time (1.5 to 3.5 minutes) did not give large fluctuations in glucose yield. A wide range of severity parameters gains high yield and therefore the optimum is broad.

For some SHS treatments the yields for xylose, arabinose, HMF and furfural (inhibitors during fermentation) are determined. Table B gives these values.

TABLE B

Yields for monosaccharides and inhibitors after SHS

| SHS Conditions | | | Yields | | | | |
|---|---|---|---|---|---|---|---|
| Temp (° C.) | Time (min) | H2SO4 (%) | Glucose (g/g DS) | Arabinose (g/g DS) | Xylose (g/g DS) | HMF* (g/g DS) | furfural* (g/g DS) |
| 160 | 1.5 | 1.5 | 0.29 | 0.02 | 0.19 | <0.001 | <0.001 |
| " | " | 2.0 | 0.27 | 0.02 | 0.19 | <0.001 | <0.001 |
| 160 | 2.5 | 1.5 | 0.29 | 0.02 | 0.19 | <0.001 | <0.001 |
| " | " | 2.0 | 0.29 | 0.01 | 0.18 | <0.001 | <0.001 |
| " | " | 3.0 | 0.31 | 0.02 | 0.19 | <0.001 | <0.001 |
| 170 | 1.5 | 2.0 | 0.32 | 0.01 | 0.21 | <0.001 | <0.001 |
| 170 | 2.5 | 1.5 | 0.27 | 0.01 | 0.17 | <0.001 | <0.001 |
| " | " | 2.0 | 0.29 | 0.01 | 0.17 | <0.001 | <0.001 |
| " | " | 3.0 | 0.28 | 0.01 | 0.15 | <0.001 | <0.001 |
| 180 | 1.5 | 2.0 | 0.29 | 0.01 | 0.19 | <0.001 | <0.001 |
| 180 | 3.5 | 0.5 | 0.19 | 0.02 | 0.16 | <0.001 | <0.001 |
| " | " | 2.0 | 0.28 | 0.01 | 0.13 | <0.001 | <0.001 |
| 190 | 1.5 | 0.5 | 0.13 | 0.02 | 0.12 | <0.001 | <0.001 |
| " | " | 2.0 | 0.28 | 0.01 | 0.17 | <0.001 | <0.001 |
| 190 | 6.5 | 0.5 | 0.17 | 0.01 | 0.13 | <0.001 | <0.001 |

*Below 0.05 g/l

The xylose content of the wheat straw was 0.19 g/g DM (method according to Cao et al., 1997). Inherent with increasing glucose yields the xylose yield increased. Almost all the xylose was recovered during optimal SHS treatments. HMF and furfural were not found in the hydrolysates. These inhibitors are volatile components and they are probably evaporated during steam treatment. The removal of these inhibitors during SHS treatment was very advantageous for the fermentation.

The combined severity factor (CSF) describes the severity of various acid-catalyzed pretreatments by combining time, temperature and acid concentration (Bower et al., 2008). It is a factor that is used widely in the art. Too low values lead to incomplete pretreatment and too high values to production of furfural and HMF from monosaccharides. The combined severity factor is given by:

$$CSF = \log_{10}\{t_r \cdot \exp[(T_r-100)/14.75]\} - pH$$

in which $T_r$ is the reaction temperature in degrees Celsius and $t_r$ is the reaction time in minutes. The pH value is calculated from the sulphuric acid concentration inside the fibers at the beginning of the treatment (pre-impregnated material).

FIG. 2 gives the glucose recovery after SHS treatment where the treatment conditions are represented by the CSF.

The glucose recovery appears to peak at a CSF between 1.5 and 2. This confirms that the optimal conditions can be found in a reasonable wide range of severity.

Besides the use of SHS for dilute acid pretreatment, SHS heating may also be interesting for thermal mild acid pretreatment. In this method lower amounts of acids are used, but longer reaction times.

Table C gives the results for optimizing SHS conditions while sulphuric acid concentrations were used comparable with thermal mild acid pretreatments (0.1-0.5% $H_2SO_4$).

TABLE C

Small scale SHS treatments, sulphate concentrations between 0.1 and 0.5%

| SHS conditions | | | After SHS treatment | | |
|---|---|---|---|---|---|
| Temp. (° C.) | Time (min) | H2SO4 (%) | H2SO4 (%) | Dry matter (%) | Glucose yield (g/g DM) |
| 180 | 3.5 | 0.1 | 2.3 | 66 | 0.11 |
| " | " | 0.5 | 3.0 | 49 | 0.19 |
| 180 | 6.5 | 0.1 | 4.7 | 91 | 0.09 |
| " | " | 0.5 | 64.6 | 98 | 0.05 |
| 190 | 1.5 | 0.1 | 2.1 | 51 | 0.08 |
| " | " | 0.5 | 2.6 | 39 | 0.13 |
| 190 | 6.5 | 0.1 | 4.4 | 90 | 0.07 |
| " | " | 0.5 | 4.1 | 64 | 0.17 |
| 160 | 15.0 | pH 2 | — | 20 | 0.23 |
| 160 | 30.0 | pH 2 | — | 22 | 0.24 |
| 160->170 (*) | 25.3 | pH 2 | — | 40 | 0.20 |

(*) 15 min 160° C., 10 min 170° C.

Thermal mild acid pretreatments comprehend high temperature and long reaction times. As a result dry matter concentrations after SHS treatment were very high which is advantageous for fermentation. However, glucose recovery was not higher than 0.17 g/g DM (50% yield). Thermal mild acid pretreatments need reaction times of >15 minutes together with temperatures around 190° C. This combination of time and temperature gives drying of the material at 6 bara operating pressure (boiling point is 159° C.). Without the presence of water the heating has no effect and reaction times >6.5 minutes and temperatures >180° C. will not enhance glucose recovery anymore.

Longer reaction times are possible if the temperature is close to the boiling point at 6 bara. Therefore 160° C. was applied together with reaction times of 15 and 30 minutes. Instead of adding a certain sulphate amount, the pH value was set to 2 during pre-impregnation of wheat straw (approximately 0.1% $H_2SO_4$). The longer reaction times gave higher glucose yield. If the temperature was raised to 170° C. after 15 minutes the yield decreased because of glucose degradation. Xylose recovery was very high (0.17 g/g DM) during heating for 15 and 30 minutes at 160° C. (not shown in the table). 15 minutes heating at 165° C. at pH of 1.5 (about 0.4% $H_2SO_4$) gave, after enzymatic hydrolysis a glucose recovery of 0.33 g/g DM).

1.1.2 Results Scaling-Up SHS Treatment

The optimal conditions for the straw substrate seemed to be 160° C.-170° C., 2.0% $H_2SO_4$ and 3.5 minutes (table B). Glucose recovery was 0.33 g/g DM which is an efficiency of 96%. These conditions were used for investigating scaling-up of the SHS pretreatment. Table D gives the results of the experiments.

TABLE D

Scaling-up SHS treatment

| | | SHS Conditions | | | After SHS treatment | |
|---|---|---|---|---|---|---|
| Configuration | Mass WS (g) | Temp. (° C.) | Time (min) | H2SO4 (%) | Dry matter (%) | Glucose yield (g/g DS) |
| Grid | 175 | 160 | 3.5 | 2 | 25.9 | 0.33 |
| Grid | 175 | 165 | 3.5 | 2 | 28.0 | 0.33 |
| Grid | 175 | 170 | 3.5 | 2 | 31.9 | 0.31 |
| Grid | 440 | 160 | 3.5 | 2 | 28.3 | 0.31 |
| Rotating basket | 258 | 160 | 3.5 | 2 | 23.5 | 0.33 |
| Rotating basket | 258 | 160 | 3.5 | 2 | 24.2 | 0.32 |

Covering the grid with 750 gram impregnated wheat straw (175 g dry matter) and no mixing gave the same efficiency (0.33 g/g DM) as reached in small scale experiments. More loading (440 g dry matter) slightly decreased the glucose recovery. Steam entered the wheat straw bed from above. While passing the bed the steam lost heat and the treatment severity decreased. A small sample placed in a basket below the wheat straw bed during treatment of the 440 g loading confirmed this. The glucose recovery for that sample was only 0.26 g/g DM.

A rotating basket was used to mix the wheat straw during heat treatment and achieve equal conditions for the complete sample. Maximal load was 1250 gram pre-impregnated wheat straw (260 gram dry matter) and glucose recovery was still 0.33 g/g DM. Xylose recovery was also high (0.18 g/g DM). The fermentation inhibitors were measured as well in the hydrolysate. It appeared that no HMF, furfural, levulinic acid and acetic acid were present. These components, coincidentally the notorious top 4 fermentation inhibitors, are probably evaporated during SHS treatment.

FIG. 3 shows that the heating up period for large scale experiments were as short as the small scale experiments.

REFERENCES

Bower S, Wickramadinghe R, Nagle N J, Schell D J (2008) Modeling sucrose hydrolyses in dilute acid solutions at the pretreatement conditions for lignocellulosic biomass. *Bioresource Technology* 99:7354-7362

Cao B, Tschirner U, Ramaswamy, S, Webb A. 1997. A rapid modified gas chromatographic method for carbohydrate analysis of wood pulps. TAPPI Journal 80(9):193-197

Example 2

Chickenfeather Biomass

SHS treated chicken feathers. Several circumstances were applied as given in table 1.

Before the chicken feathers are treated with super heated steam the feathers are pretreated by soaking the feathers 3 hours at 50° C. in a 0.1 M sodium hydroxide solution. After the soaking the feathers were cooled down to room temperature and dried overnight.

TABLE 1

| Method | 1 | 2 | 3 | 4 | 5 |
|---|---|---|---|---|---|
| Pressure | 4 | 2 | 3 | 5 | 5 |
| Temperature (° C.) | 160 | 120 | 143 | 160 | 160 |
| Flow | 160-180 | 160-180 | 160-180 | 160-180 | 160-180 |
| Time (min) | 10 | 10 | 10 | 10 | 5 |
| Weight (g) | 300 | 300 | 300 | 300 | 300 |
| After drying (g) | 270 | 300 | 290 | 275 | 250 |
| Moisture (%) | 69.9 | 65.2 | 69.0 | 65.2 | 63.4 |

Experiment 1

In 100 ml of water containing 2.5 g of calcium hydroxide 7.5 g (dry weight) of SHS treated chicken feathers according to method 5 were added. The mixture is heated to 50° C. After 7 hours the heating is switched of and the mixture is allowed to stir overnight. Then 30% hydrogen peroxide (5 ml) is added and the mixture is brought to pH 7 using dry ice, filtered and concentrated to 15 ml containing 50% dry weight protein.

Experiment 2

In 100 ml of water containing 2.5 g of calcium hydroxide 7.5 g (dry weight) of SHS treated chicken feathers according to method 5 were added. The mixture is heated to 70° C. After 7 hours the heating is switched of and the mixture is allowed to stir overnight. Then 30% hydrogen peroxide (5 ml) is added and the mixture is brought to pH 7 using dry ice, filtered and concentrated to 15 ml containing 50% dry weight protein.

Experiment 3

In 100 ml of water containing 2.5 g of calcium hydroxide 7.5 g (dry weight) of SHS treated chicken feathers according to method 3 were added. The mixture is heated to 60° C. After 7 hours the heating is switched of and the mixture is allowed to stir overnight. Then 30% hydrogen peroxide (5 ml) is added and the mixture is brought to pH 7 using dry ice, filtered and concentrated to 15 ml containing 50% dry weight protein.

Experiment 4

In 100 ml of water containing 2.5 g of calcium hydroxide 7.5 g (dry weight) of SHS treated chicken feathers according to method 2 were added. The mixture is heated to 70° C. After 7 hours the heating is switched of and the mixture is allowed to stir overnight. Then 30% hydrogen peroxide (5 ml) is added and the mixture is brought to pH 7 using dry ice, filtered and concentrated to 15 ml containing 50% dry weight protein.

Experiment 5

In 100 ml of water containing 2.5 g of calcium hydroxide 7.5 g (dry weight) of SHS treated chicken feathers according to method 4 were added. The mixture is heated to 50° C. After 7 hours the heating is switched of and the mixture is allowed to stir overnight. Then 30% hydrogen peroxide (5 ml) is added and the mixture is brought to pH 7 using dry ice, filtered and concentrated to 15 ml containing 50% dry weight protein.

Experiment 6

In 100 ml of water containing 2.5 g of calcium hydroxide 7.5 g (dry weight) of SHS treated chicken feathers according to method 1 were added. The mixture is heated to 50° C. After 7 hours the heating is switched of and the mixture is allowed to stir overnight. Then 30% hydrogen peroxide (5 ml) is added and the mixture is brought to pH 7 using dry ice, filtered and concentrated to 15 ml containing 50% dry weight protein.

Experiment 7

In 100 ml of water containing 2.5 g of calcium hydroxide 7.5 g (dry weight) of SHS treated chicken feathers according to method 5 were added. The mixture is heated to 80° C. After 7 hours the heating is switched of and the mixture is allowed to stir overnight. Then 30% hydrogen peroxide (5 ml) is added and the mixture is brought to pH 7 using dry ice, filtered and concentrated to 15 ml containing 50% dry weight protein.

Enzymatic Hydrolysis of SHS Treated Chicken Feathers

SHS treated chicken feathers, treated according to method 5 100 ml of water was added and the solution was brought to pH 9.2. Then the suspension was brought to 50° C. and 0.5 of a savinase solution was added. The pH was kept at 9.2 during the hydrolysis. After 2.5, 5, and 24 hours the hydrolysis was stopped by bringing the pH to neutral and the samples were filtered and the amount of feathers in grams was measured. In table 2 the results are given. As a blank experiment also feathers that were alkali treated but have not been put under SHS conditions was measured.

TABLE 2

|  | SHS treated | Alkaline |
|---|---|---|
| 2.5 hours | 5.7 | 9.7 |
| 5 hours | 4.5 | 9.7 |
| 24 hours | 3.2 | 6.6 |
| Non enzymatic treated feathers |  | 10.0 |

Example 3

Derivation of Process Products

Example 3a

Acylation (Pre)-treated straw was acetylated according to Rodrigues Filho et al. (2005).

The product data are summarised in Table 3.

Glacial acetic acid (40 mL) was added to (pre)-treated straw (2 g). The mixture was stirred during 30 minutes at room temperature. A solution of 0.3 mL $H_2SO_4$ and 17.5 mL glacial acetic acid was added to the mix, after which it was stirred for 15 minutes at room temperature. The mixture was filtrated and the straw was returned into the initial flask. To the filtrate, 40 mL acetic anhydride was added. The acidic solution was mixed and added to the straw. The mixture was stirred for 30 minutes and left to stand for 1, 5 and 21 hours. Water (400 mL) was added and the solution was desalted using a membrane filter (MWCO 3500). Finally, the solution was freeze-dried and the product was analysed. The degree of substitution was determined by pretreating a sample by dissolving in water for free acid and in 0.5 M NaOH for total acid analysis. The sample was analysed using HPLC (column Aminex HPX-87H 300 mm×7.8 mm, eluent 0.01 M sulphuric acid, and RI detection).

TABLE 3

Acetylated straw (degree of substitution - DS - per anhydroglucose unit)

| Straw | 1 hour | 5 hours | 21 hours |
|---|---|---|---|
| Original | 0.3 | 0.6 | 2.1 |
| Pre-treated with 2% H2SO4 | 1.4 | 1.6 | 2.2 |
| Pre-treated with 2% H2SO4 and SHS | 1.8 | 1.8 | 2.2 |

Example 3b

Carboxymethylation a. first step; pre-drying
Straw predried at 90° C. for 12 h
b. second step; sulfuric acid pre-treatment
To 10 liters of (2% (w/w) or pH 2), 900 g (dry solid) pre-dried straw is applied for 3 h at 60° C. Afterwards the straw is dried until a dry solid content of approximately 30%.
c. third step; SHS
A certain amount of sulfuric acid pre-treated straw is applied under superheated steam conditions for a certain amount of time and Temperature Table 4). Solid matter is approximately 20-25% after SHS

TABLE 4

| Concentration | Steam flow | P (atm) | Time (min) | Temp. |
|---|---|---|---|---|
| 2% | 180 kg/hr | 6 | 3.5 | 160° C. |
| pH 2 | 180 kg/hr | 6 (atm) | 3.5 | 160° C. |

Example 3b-2

Carboxymethylation: Impact Sulphuric Acid Treatment

A solution is prepared of 140 g isopropanol, 15.4 g water and 7.8 g NaOH (50%). To this, 32.5 g sulphuric acid pre-treated straw is added. Then 5.6 gr mono-chloric acetic acid is added. The mixture is stirred for 1 hour at 70 C. The reaction is ended by addition of citric acid/ethanol until a pH is reached of approximately 7.

Then the mixture is centrifuged. To the residue demineralised water is added till a volume of 140 ml which is added to 420 ml ethanol (100%). The mixture is filtered over a Buchner funnel and washed with 100 ml water. Afterward the filtrate is dried at 60° C. in an oven till the moisture content is between 10-20%.

Swelling capacity was determined.

Example 3b-3

Carboxymethylation: Impact SHS+Water

A solution is prepared of 140 g isopropanol, 15.4 g water and 7.8 g NaOH (50%). To this, 32.5 g SHS (water) pre-treated straw is added. Then 5.6 g monochloric acetic acid is added. The mixture is stirred for 1 hour at 70° C. The reaction is ended by addition of citric acid/ethanol until a pH is reached of approximately 7.

Then the mixture is centrifuged. To the residue demineralised water is added till a volume of 140 ml which is added to 420 ml ethanol (100%). The mixture is filtered over a Buchner funnel and washed with 100 ml water. Afterward the filtrate is dried at 60° C. in an oven till moisture content between 10-20%.

Swelling capacity was determined.

Example 3b-4

Carboxymethylation: Impact Sulphuric Acid Treatment and SHS

A solution is prepared of 140 g isopropanol, 15.4 g water and 7.8 g NaOH (50%). To this, 32.5 g sulphuric acid/SHS pre-treated straw is added. Then 5.6 g monochloric acetic acid is added. The mixture is stirred for 1 hour at 70 C. The reaction is ended by addition of citric acid/ethanol until a pH is reached of approximately 7.

Then the mixture is centrifuged. To the residue, demineralised water is added till a volume of 140 ml which is added to 420 ml ethanol (100%). The mixture is filtered over a Buchner funnel and washed with 100 ml water. Afterward the filtrate is dried at 60° C. in an oven till dry solid content between 10-20%.

Swelling capacity was determined.

Example 3b-5

Carboxymethylation: Influence Degree of Substitution

A solution is prepared of 140 g isopropanol, 15.4 g water and 4 g NaOH (50%). To this, 21 g sulfuric acid/SHS pre-treated straw is added. Then 5.7 or 2.88 or 1.44 gr mono-chloric acetic acid is added. The mixture is stirred for 1 hour at 70 C. The reaction is ended by addition of citric acid/ethanol until a pH is reached of approximately 7.

Then the mixture is centrifuged. To the residue, demineralised water is added till a volume of 140 ml which is added to 420 ml ethanol (100%). The mixture is filtered over a Buchner funnel and washed with 100 ml water. Afterward the filtrate is dried at 60 C. in an oven until a moisture content between 10-20%.

Swelling capacity was determined.

TABLE 5

Result of experiments 3b-1 to 3b-5

| sample | $H_2SO_4$ | SHS | Swelling capacity ml/g |
|---|---|---|---|
| 032 | 0 | 3.5 min | 33 |
| 038-2 | pH 2 | | 26 |
| 038-3 | pH 2 | 3.5 min | 34 |
| 021 | 2% | — | 10 |
| 022 | 2% | 3.5 min | 40 |
| 024 | 2% | 3.5 min | 34 |

| Sample number | $H_2SO_4$ % | SHS | Reaction T 70° C. | MCA·Na g | Reaction time 70° C. | Swelling capacity ml/g | swelling on load |
|---|---|---|---|---|---|---|---|
| 036 | 2 | 3.5 min | 1 hour | 5.76 | 20 h | 50 | 6.6 |
| 037-1 | 2 | 3.5 min | 1 hour | 2.88 | 20 h | 59 | 7.4 |

The invention claimed is:

1. A method for processing biomass derived from plants or animals to make available saccharides and proteins therein for further processing, comprising the steps of:
   a. pre-treating said biomass material containing lignocellulose with an aqueous solution of acid or base to hydrolyze the saccharides from the lignocellulose or the proteins from the biomass material; and
   b. subsequently passaging super heated "SHS" steam at an elevated pressure through a pressure chamber containing said pre-treated biomass material to further increase the separation of the saccharides from the lignocellulose or the proteins from the biomass material;

wherein the water activity "Aw" of the super heated steam is controlled by means of temperature and pressure of the super heated steam to be less than 1 and is defined by the formula $$Aw = PSHS/P_{saturated\ steam} \text{ at } T_{SHS} \text{ with } P=\text{absolute pressure,}$$

and wherein the super heated steam is applied for at least 1 minute and less than 30 minutes.

2. The method according to claim 1, wherein the acid is sulfuric acid ($H_2SO_4$) or the base is chosen from the group consisting of calcium hydroxide, sodium hydroxide and potassium hydroxide, ammonium hydroxide or wherein the acid or base is any in situ formed acid or base.

3. The method according to claim 2, wherein the acid is provided in a solution of 0.1% to 4.0%.

4. The method according to claim 2, wherein the base is mixed with the biomass in a ratio of 0.02 to 0.2 grams base per gram biomass.

5. The method according to claim 1, wherein step a) is performed at a temperature of 20 to 80° C.

6. The method according to claim 1, wherein the super heated steam is applied under a pressure between 1 and 10 bars.

7. The method according to claim 1, wherein the temperature of the super heated steam is between 150 and 220° C.

8. The method according to claim 1, wherein the process comprises a further step c) of further enzymatic hydrolysis (exo and endo activity), acylation, oxidation, etherification, carboxymethylation or esterification of said material after super heated steam treatment.

9. The method according to claim 8, wherein step c) comprises acylation or carboxymethylation.

10. The method according to claim 1, wherein the material is woody plant material, including leaves, twigs, bark, grasses, hay, reeds, megasse, straw, wood chips, sawdust, bagasse, corn stover, corn cobs, wheat bran, sugar beet press cake, rice hulls, palm, coconut, cotton fibres and/or peat, sphagnum, filtercake from sewage plants, sewage effluents, animal waste, like feathers and hairs, or crystalline cellulose.

11. The method according to claim 1, wherein the saccharides are polysaccharides.

12. The method according to claim 11, wherein the process comprises a further step c) of applying an enzyme to process the polysaccharides into oligo- and monosaccharides.

13. The method according to claim 1, wherein the super heated steam is applied to the biomass for less than 15 minutes.

14. The method according to claim 13, wherein the super heated steam is applied to the biomass for 1 to 10 minutes.

15. A method for processing biomass derived from plants or animals to make available saccharides and proteins therein for further processing, comprising the steps of:
 a. pre-treating said biomass material containing lignocellulose with an aqueous solution of acid or base to hydrolyze the saccharides from the lignocellulose or the proteins from the biomass material; and
 b. subsequently passaging super heated "SHS" steam at an elevated pressure through a pressure chamber containing said pre-treated biomass material to further increase the separation of the saccharides or the proteins from the biomass material;

wherein the water activity "Aw" of the super heated steam is controlled by means of temperature and pressure of the super heated steam to be less than 1 and is defined by the formula $Aw=P_{SHS}/P_{saturated\ steam}$ at $T_{SHS}$ with P=absolute pressure, and the temperature of the super heated steam is between 150 and 220° C., and wherein the super heated steam is applied for at least 1 minute and less than 30 minutes.

16. The method according to claim 1, wherein the temperature of the super heated steam is between 160 and 220° C.

17. The method according to claim 15, wherein the process further comprises step c) of further enzymatic hydrolysis (exo and endo activity), acylation, oxidation, etherification, carboxymethylation or esterification of said biomass material after super heated steam treatment.

18. The method according to claim 15, wherein the process further comprises step c) of applying an enzyme to said biomass material to process polysaccharides separated from said lignocellulose into oligo- and monosaccharides.

19. The method according to claim 1, further comprising the step of:
 c. opening said pressure chamber thereby allowing said pressure in said pressure chamber to return to atmospheric pressure and allowing said pre-treated biomass material within said pressure chamber to cool.

20. The method according to claim 15, further comprising the step of:
 c. opening said pressure chamber thereby allowing said pressure in said pressure chamber to return to atmospheric pressure and allowing said pre-treated biomass material within said pressure chamber to cool.

* * * * *